United States Patent
Roeder

(10) Patent No.: US 10,350,096 B2
(45) Date of Patent: Jul. 16, 2019

(54) EXPANDABLE STENT-GRAFT SYSTEM HAVING DIAMETER REDUCING CONNECTORS

(71) Applicant: Cook Medical Technologies LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1300 days.

(21) Appl. No.: 13/828,402

(22) Filed: Mar. 14, 2013

(65) Prior Publication Data

US 2014/0180378 A1 Jun. 26, 2014

Related U.S. Application Data

(60) Provisional application No. 61/746,036, filed on Dec. 26, 2012.

(51) Int. Cl.

| | |
|---|---|
| *A61F 2/95* | (2013.01) |
| *A61F 2/966* | (2013.01) |
| *A61F 2/07* | (2013.01) |
| *A61F 2/06* | (2013.01) |

(52) U.S. Cl.
CPC .............. *A61F 2/95* (2013.01); *A61F 2/07* (2013.01); *A61F 2/966* (2013.01); *A61F 2002/065* (2013.01); *A61F 2002/067* (2013.01); *A61F 2002/9511* (2013.01)

(58) Field of Classification Search
CPC ...... A61F 2/07; A61F 2/95; A61F 2002/9505; A61F 2002/9511; A61F 2002/065; A61F 2002/067
See application file for complete search history.

(56) References Cited

U.S. PATENT DOCUMENTS

| | | | |
|---|---|---|---|
| 7,722,657 | B2 | 5/2010 | Hartley |
| 7,803,177 | B2 | 9/2010 | Hartley et al. |
| 7,993,383 | B2 | 8/2011 | Hartley et al. |
| 2004/0138734 | A1* | 7/2004 | Chobotov ............... A61F 2/954 623/1.11 |

(Continued)

FOREIGN PATENT DOCUMENTS

EP 1 136 044 A1 9/2001

*Primary Examiner* — Sarah A Simpson
(74) *Attorney, Agent, or Firm* — Brinks Gilson & Lione

(57) ABSTRACT

A system for deploying a stent-graft within a body vessel is provided. The system includes an expandable stent-graft having expandable stent rings attached thereto and a cannula extending through the stent-graft. The system includes a plurality of diameter reducing connectors extending around the circumference of the graft for reducing the diameter of the graft. The system further includes a plurality of trigger wires extending longitudinally along the perimeter of the graft. The trigger wires extend through the diameter reducing connectors to constrain the connectors for reducing the diameter of the stent-graft. The trigger wires are also releasably attached to the apices of a bare stent portion extending from the proximal end of the graft body. The trigger wires can be sequentially retracted to release the bare stent and the diameter reducing connectors to expand the stent-graft radially into engagement with the wall of the body vessel.

9 Claims, 7 Drawing Sheets

(56) References Cited

U.S. PATENT DOCUMENTS

| | | |
|---|---|---|
| 2006/0004433 A1 | 1/2006 | Greenberg et al. |
| 2007/0043425 A1* | 2/2007 | Hartley ............... A61F 2/07 623/1.12 |
| 2007/0083255 A1* | 4/2007 | Chiang ............... A61F 2/07 623/1.11 |
| 2008/0294234 A1 | 11/2008 | Hartley et al. |
| 2009/0204202 A1 | 8/2009 | Dierking et al. |
| 2011/0118816 A1* | 5/2011 | Jensen ............... A61F 2/07 623/1.11 |
| 2011/0125244 A1 | 5/2011 | Roeder et al. |
| 2012/0172965 A1 | 7/2012 | Kratzberg et al. |
| 2012/0239130 A1 | 9/2012 | Hartley et al. |

* cited by examiner

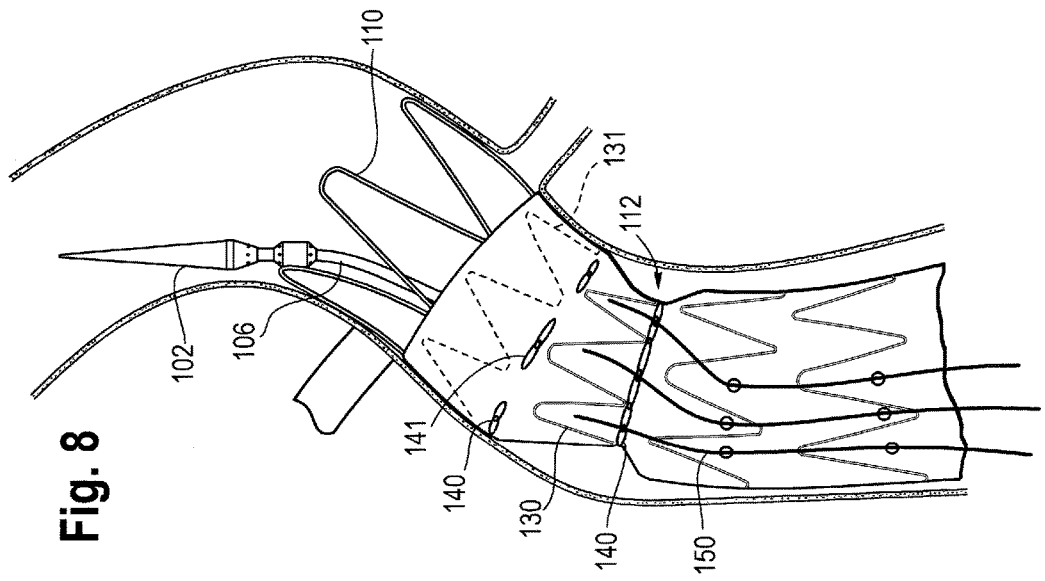
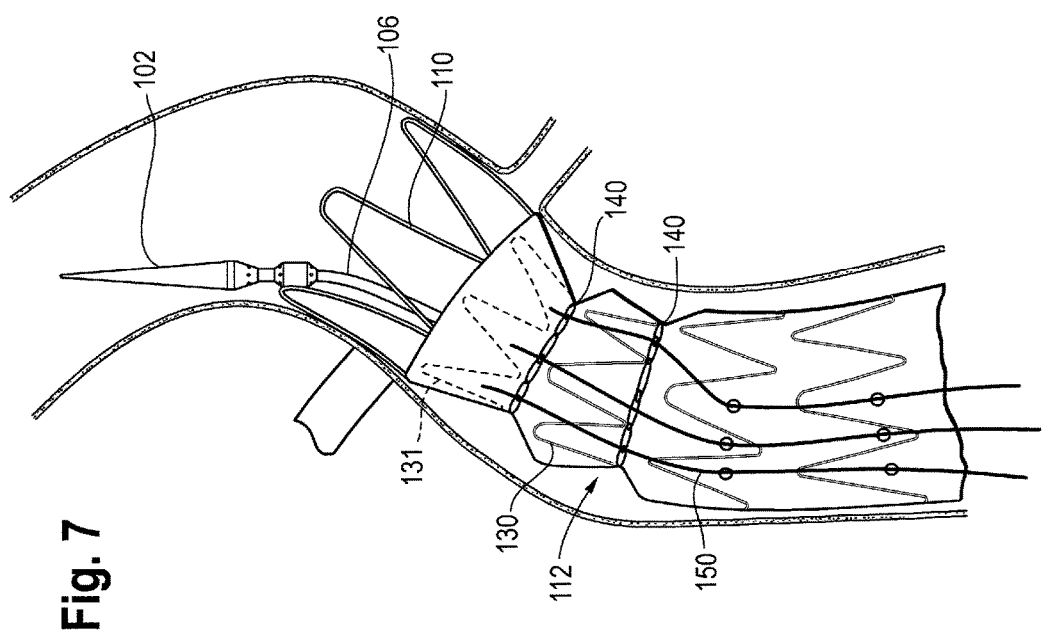

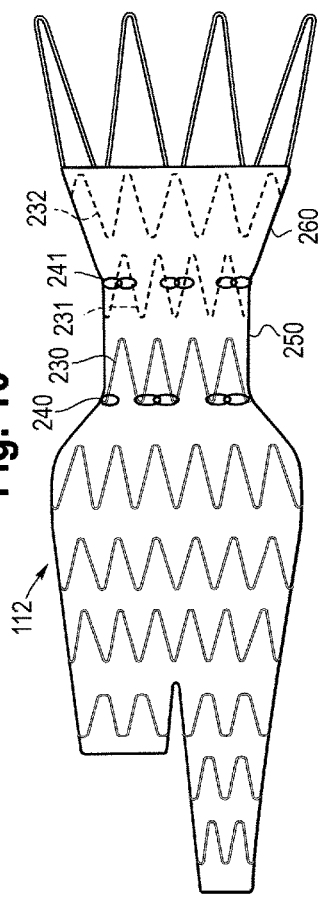
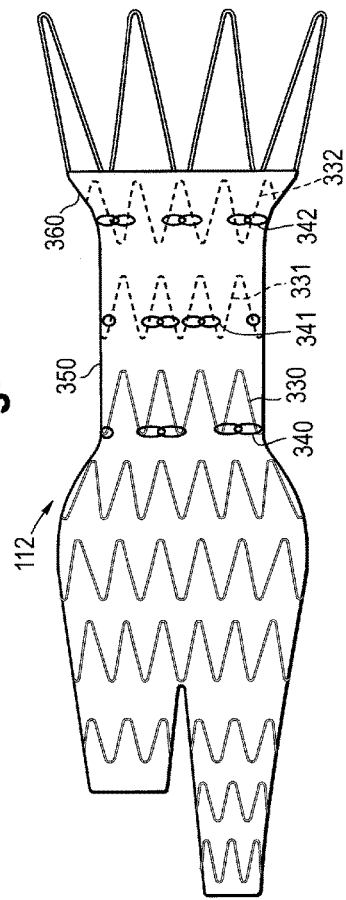
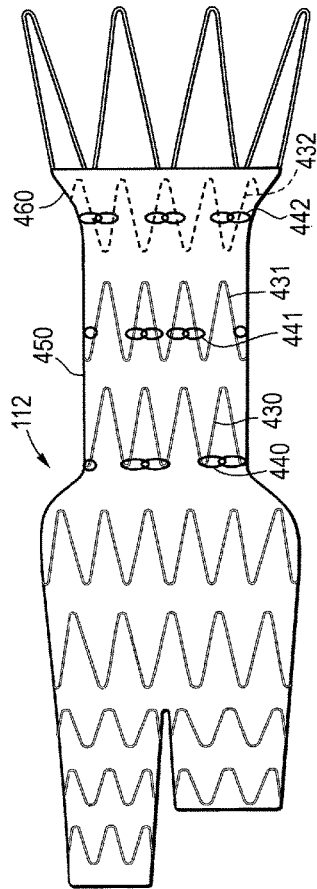

EXPANDABLE STENT-GRAFT SYSTEM HAVING DIAMETER REDUCING CONNECTORS

CROSS-REFERENCE TO RELATED APPLICATIONS

This application claims the benefit of U.S. Provisional Application No. 61/746,036, filed Dec. 26, 2012, entitled "EXPANDABLE STENT-GRAFT SYSTEM HAVING DIAMETER REDUCING CONNECTORS," the entire contents of which are incorporated by reference herein.

BACKGROUND

1. Field of the Invention

This invention relates to medical devices and, in particular, to a delivery system for an endoluminal prosthesis and method of deploying the endoluminal prosthesis.

2. Description of Related Art

Endoluminal prostheses, such as stents and stent grafts, are used for treating damaged or diseased body lumens such as the aorta and the thoracic arch.

Endovascular Repair of thoracic pathologies is an effective, non-invasive treatment option that has gained tremendous popularity over the last 10 years. However, challenging anatomy, such as highly curved or tortuous anatomy often times leads to a non-ideal device deployment where the endovascular graft does not fully conform to the inner curvature of the vasculature. This complication can occur if the device is deployed from its compressed state in a non-controlled manner. This complication can and has led to device failures including; device migration, stent fatigue/fracture, endoleaks, etc. One type of stent-graft includes a bare stent at the proximal end for anchoring the stent to limit migration, with the bare stent being commonly constrained by trigger wires that extend within the graft for being withdrawn therethrough to release the bare stent. However, these trigger wires are generally thick to firmly hold the bare stents, and thereby increase the overall profile of the device. Accordingly, it has become apparent to the inventors that an improved system for delivering endoluminal prostheses, such as stent-grafts, is desirable.

SUMMARY

Delivery systems for deploying endovascular prostheses, such as stent-grafts, are described which may be readily conformable to a patient's anatomy, for example, the aortic or thoracic arch, to allow for more accurate placement thereof. The embodiments may include any of the following aspects in various combinations and may also include any other aspect described below in the written description or in the attached drawings.

In one form a system for deploying a stent-graft is provided, the system comprising: an expandable stent-graft comprising: a proximal end; a distal end; a lumen extending from the proximal end to the distal end; a tubular graft having a proximal portion including a proximal end, an intermediate portion, and a distal portion including a distal end; a stent ring attached to the perimeter of the graft; a releasable diameter reducing connector extending around the stent ring; a releasable stent portion extending from at least one of the proximal and distal ends at least partially axially from an end having apices at a proximal end thereof; a retractable trigger wire disposed adjacent a surface of the stent-graft extending longitudinally along the length of the stent-graft, the trigger wire releasably attached to the releasable diameter reducing connector and the releasable stent portion.

In another form, the trigger wire is attached to the graft along its length.

In another form, the system further comprises a cannula extending from a distal end to a proximal end, wherein the cannula extends within the lumen of the stent-graft and the trigger wire is releasably attached to a proximal portion of the cannula and attached to a distal portion of the cannula.

In another form, the diameter reducing connector includes a plurality of loops.

In another form, the trigger wire extends through two of the plurality of loops.

In another form, wherein the trigger wire is longitudinally threaded through the graft along its length.

In another form, the diameter reducing connector extends around a distal portion of the stent ring.

In another form, the diameter reducing connector extends around a middle portion of the stent ring.

In another form, the diameter reducing connector extends around a proximal portion of the stent ring.

In another form, a stent-graft apparatus is provided comprising: a tubular graft having a proximal portion including a proximal end, an intermediate portion, and a distal portion including a distal end; a first stent ring attached to the perimeter of the graft; a first releasable diameter reducing connector extending around the first stent ring; a second stent ring attached to the perimeter of the graft; and a second diameter reducing connector extending around the second stent ring; a releasable stent portion extending from at least one of the proximal and distal ends; a retractable trigger wire disposed adjacent a surface of the grant and extending longitudinally along the length of the graft, the trigger wire releasably attached to the first and second releasable diameter reducing connectors and the releasable stent portion.

In another form, the tubular graft surrounds the first stent ring, the second stent ring surrounds the tubular graft, and the second stent ring is disposed distally from the first stent ring.

In another form, the graft includes a proximal portion, a first distal leg portion, and second distal leg portion.

In another form, the trigger wire extends longitudinally along the first distal leg portion.

In another form, the first distal leg portion is longer than the second distal leg portion.

In another form, the apparatus further comprises a third diameter reducing connector attached to the proximal end of the graft and adjacent a distal end of the bare stent.

In another form, a method for delivering a stent-graft to a body vessel is provided, the method comprising: delivering, in a compressed condition, an expandable stent-graft system to a body vessel, the system including an expandable stent-graft comprising: a proximal end; a distal end; a lumen extending from the proximal end to the distal end; a tubular graft having a proximal portion including a proximal end, an intermediate portion, and a distal portion including a distal end; a stent ring attached to the perimeter of the graft; a releasable diameter reducing connector extending around the stent ring; a releasable stent portion extending from at least one of the proximal and distal ends; a retractable trigger wire disposed adjacent a surface of the stent-graft and extending longitudinally along the length of the stent-graft, the trigger wire releasably attached to the releasable diameter reducing connector and the releasable stent portion; withdrawing the trigger wire a first longitudinal distance along the length of the stent-graft; in response to withdrawing the trigger wire a first longitudinal distance, releasing the releasable stent portion to expand the bare stent portion in a radial direction and toward engagement with a wall of the body vessel; in response to releasing the releasable bare stent portion, withdrawing the trigger wire a second longitudinal distance along the length of the stent-graft; in response to withdrawing the trigger wire a second longitudinal distance, releasing the stent ring to expand the stent ring in a radial direction toward engagement with the wall of the body vessel.

In another form, the stent-graft system further comprises a cannula having proximal and distal ends and extending through the stent graft lumen, the trigger wire is releasably attached to the proximal end of the cannula, and the trigger wire constrains the releasable stent portion in the compressed condition.

In another form, the diameter reducing connector comprises a plurality of loops, the trigger wire extends through a pair of the plurality of loops to constrain the diameter reducing connector, and withdrawing the trigger wire releases at least one pair of the plurality of loops to allow the stent ring to expand radially outward toward the wall of the body vessel.

In another form, the stent-graft further comprises a pair of distal leg portions, the trigger wire extends longitudinally along the length of one of the distal leg portions, and the trigger wire is withdrawn longitudinally along the length of the one of the distal leg portions.

In another form, the trigger wire is attached to the graft via an attachment therebetween, and the trigger wire is withdrawn through the attachment.

The foregoing paragraphs have been provided by way of general introduction, and are not intended to limit the scope of the following claims. The described embodiments will be best understood by reference to the following detailed description taken in conjunction with the accompanying drawings.

BRIEF DESCRIPTION OF THE DRAWINGS

The embodiments described below may be more fully understood by reading the following description in conjunction with the drawings, in which:

FIGS. 5-9 illustrate the staged deployment of the stent-graft within a body vessel with the trigger wires being withdrawn distally to release the bare stents and the diameter reducing connectors.

FIG. 10 illustrates another embodiment of a stent graft;

FIG. 11 illustrates yet another embodiment of a stent graft; and

FIG. 12 illustrates yet another embodiment of a stent graft.

DETAILED DESCRIPTION

Throughout this specification, the terms "distal" and "distally" refer to a position, direction, or orientation that is generally away from the heart. Accordingly, the terms "proximal" and "proximally" refer to a position, direction, or orientation that is generally toward, or closer to the heart.

The terms "endoluminal device" and "endovascular device" refer to or describe objects that can be placed inside a vessel, a lumen or a body passageway in a human or animal body. A lumen, vessel, or a body passageway can be a naturally occurring lumen or a lumen created by surgical intervention. As used in this specification, the terms "lumen" or "body passageway" are intended to have a broad meaning and encompasses any duct (e.g., natural or iatrogenic) within the human body and can include blood vessels, respiratory ducts, gastrointestinal ducts, and the like. Thus, "Endoluminal devices" or "endoluminal prosthesis" describe devices that can be placed inside one of these lumens.

The term "fenestration" refers to an opening in a structure through which fluid can pass. The term "fenestration window" refers to a portion of a device comprising a substantially fluid impenetrable covering through which a fenestration can be opened or created by piercing, cutting, tearing, or the like.

The term "stent" means any device or structure that adds rigidity, expansion force or support to a prosthesis or body lumen. A stent is used to obtain and/or maintain the patency of the body passageway while maintaining the integrity of the passageway. In addition, the stent may be used to form a fluid seal against the body lumen. The stent may be coated with a polymeric material, for example, by immersion in liquid polymer or any other method known to one of skill in the art. The stent may be located on the exterior of the device, the interior of the device, or both. A stent may be self-expanding, balloon-expandable or may have characteristics of both.

The term "graft" or "graft material" describes an object, device, or structure that is joined to or that is capable of being joined to a body part to enhance, repair, or replace a portion or a function of that body part. A graft by itself or with the addition of other elements, such as structural components, e.g. stents, can form an endoluminal/endovascular device commonly referred to as a "stent-graft." The graft may comprise a single material, or a composite blend of materials. These materials may be in the form of a woven fabric, a laminate, etc. Throughout this specification, like reference numbers refer to like elements.

Figure 1:
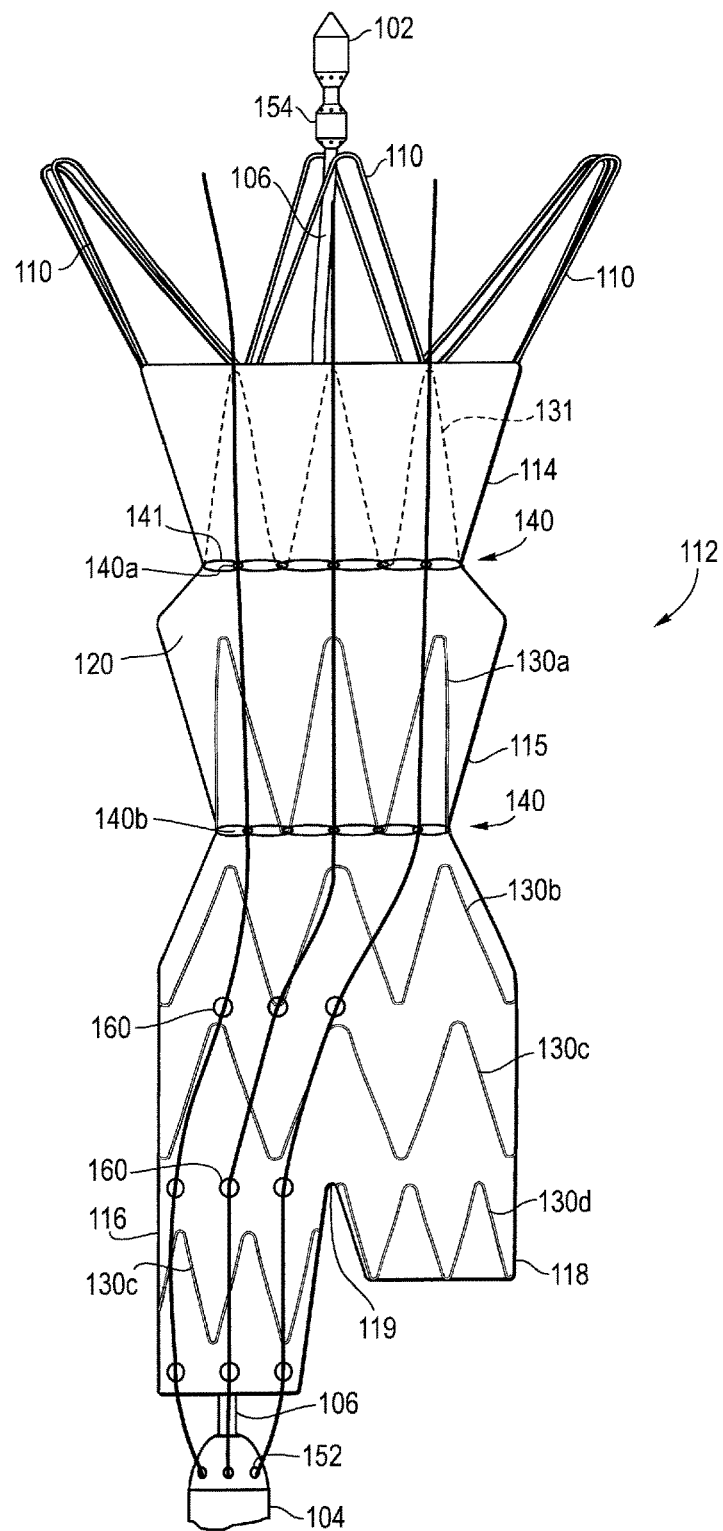
FIG. 1 is a front view of a stent-graft having a bare stent portion in an open position and a plurality of trigger wires extending along the exterior of the stent-graft constraining first and second diameter reducing connectors.
Figure 2:
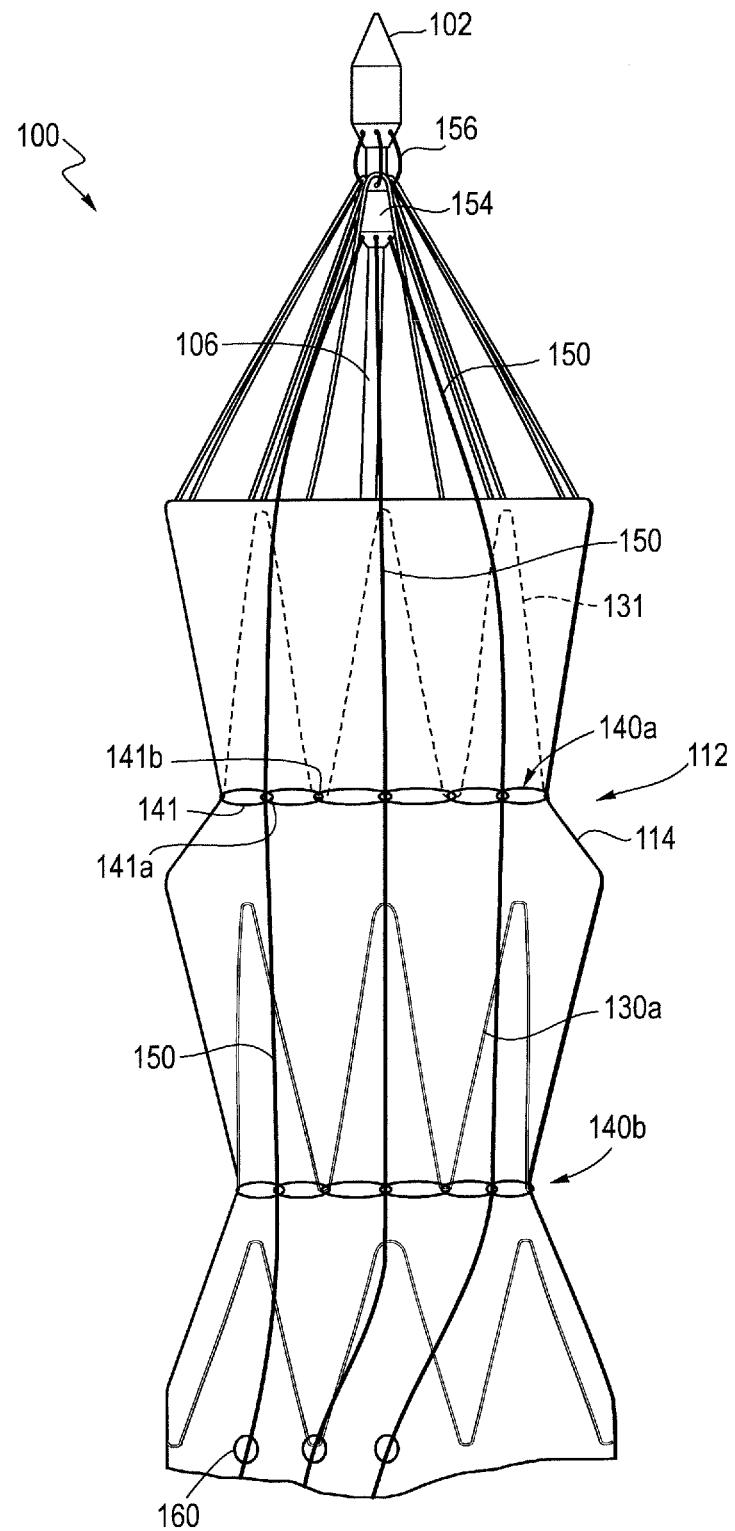
FIG. 2 is a front view of the stent graft showing the bare stents being constrained at their proximal ends by the trigger wires.

Referring now to the figures, FIGS. 1 and 2 illustrate an embodiment of a delivery system 100 including a dilator or nose cone 102 disposed at a proximal end thereof. The nose cone 102 is attached to a proximal end of a cannula 106, and the distal end of the cannula 106 is attached to a catheter 104. An endoluminal prosthesis 112, which is shown in this embodiment as a stent-graft, is disposed about the cannula 106. The stent-graft 112 can be in the form of a bifurcated body, with a main proximal portion 114, an intermediate portion 115, a first distal leg portion 116 and a second distal leg portion 118. The distal leg portions 116 and 118 extend distally from a bifurcation point 119 disposed near the distal end of the intermediate portion 115.

The stent-graft 112 includes a tubular graft material 120 attached to a support frame or structure comprising a plurality of stents 130, 131 having an undulating or zigzag configuration that comprising a plurality of structural members connected together at their ends by bends. The stents 130, 131 may be formed from a single wire made of Nitinol, stainless steel, polymers, or other materials having elastic or super elastic properties. Alternatively, the stents 130, 131 may be cut from a cannula or the like. While the stents 130, 131 are shown in the Figures as comprising individual, discreet stent rings 130a, 130b, 130c, 130d, etc. that are spaced in intervals along the length of the graft 120, in another embodiment the stent rings may be formed as a single monolithic structure that extends and wraps around the graft 120 in a helical shape from the proximal end of the graft 120 to the distal end of the graft 120.

The stent 131 can be in the form of a proximal sealing stent 131 and disposed at the proximal portion 114 and along the internal surface of the stent-graft 112, so that the proximal portion 114 can be generally free from stent structure on the outer surface. The stents 130 can be disposed around the remainder of the stent-graft 112 on the exterior surface thereof so that the stents 130 are exposed. The stents 130 can have a generally sharp construction, if desired, to promote tissue ingrowth of the stents 130 when the stent-graft 112 has been installed, thereby limiting migration of the stent-graft 112.

The stent-graft 112 can further include a plurality of bare stents 110 extending from the proximal end of the stent-graft 112. The bare stents 110 can be made of a material similar to the stents 130 and 131. The bare stents 110 are biased to spring outward upon release from a compressed or constrained condition, as further described below, for assisting in the installation of the stent-graft 112 within the anatomy. The outward force of the bare stents 110 exerts a force on the body cavity, thereby limiting instances of the migration of the stent-graft 112 and acting as an anchor for the stent-graft 112 during installation.

In another form, the bare stents 110 can extend from the distal end of the stent-graft 112.

Returning to FIG. 1, a plurality of diameter reducing connectors 140, which may be formed by a plurality of loops 141 defined by sutures, wire loops or the like, are attached to the bends of the stents 130, 131 and may also be attached to the graft material 120. In one embodiment, the diameter reducing connectors 140a are attached to the circumferentially adjacent distal bends of the proximal sealing stent 131, and the connectors 140b are attached to the circumferentially adjacent distal bends of the stent 130a that is longitudinally adjacent the proximal sealing stent 131.

Figure 3:
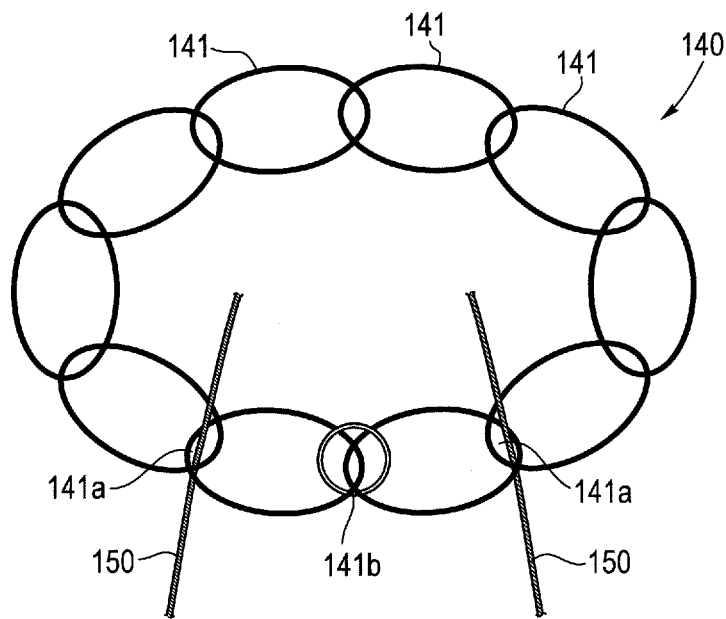
FIG. 3 is a top view of one of the diameter reducing connectors.

With reference to FIG. 3, the connector 140 comprises the loops 141. The loops 141 can be coupled to each other at ends 141a and 141b. The loops 141 at point 141b can be attached to the graft material 120 to hold one end of the loop 141 to the stent-graft 112. The loop 141 at end 141a can be coupled to the adjacent loop 141 via a trigger wire 150 extending through the ends 141a of adjacent loops 141. As will be further described below, when the trigger wire 150 is retracted distally from the loops 141 of the connector 140, the loops 141 will be de-coupled from each other and allow the stent-graft 112 to expand at that location.

The connectors 140 can, in other embodiments, be attached to additional stents 130 along the length of the stent-graft 112, if desired. In another form, the connectors 140 can be attached at the proximal end of the stent-graft 112 to the bare stents 110 or the proximal bends of the sealing stent 131.

While the connectors 140 have been described as being attached, generally, to the distal bends of the stents 130 and 131, the connectors could be attached to the middles of the stents 130 and 131, approximately halfway in between the proximal and distal bends of the stents 130 and 131. By attaching to either the distal bends or the proximal bends, the stents 130 and 131 can be compressed a greater amount than the bends at the opposite longitudinal end of the stent. By attaching to the middle, the stents 130 and 131 can be compressed relatively equally between the proximal and distal bends thereof.

Note that while only one side of the stent-graft 112 is shown in FIGS. 1 and 2, the deployment device 100 is constructed in a similar manner on the opposite side that is not shown.

With reference again to FIGS. 1 and 2, the stent-graft 112 further includes a plurality of triggers wires 150 that extend in a generally longitudinal direction along the perimeter of the stent-graft 112. The trigger wires 150 may be a suture, a wire made from a titanium alloy, such as Nitinol, or other flexible elongate mono or multifilament member of suitable tensile strength. The trigger wires 150 can extend from a distal handle (not shown) through a lumen of the catheter 104 and exiting the catheter at holes 152, where they can then extend along the circumferential perimeters of the distal leg 116, the intermediate portion 115, and the proximal portion 114. The trigger wires 150 can further extend into the nose cone 102.

More specifically, the trigger wires 150 can be routed into a housing 154 located at the proximal end of the cannula 106 and distally from the nose cone 102. The wires 150 then extend out of the housing 154, before entering the interior of the nose cone 102, where the proximal ends of the trigger wires 150 will terminate.

The extension of the trigger wires 150 between the housing 154 and the nose cone 102 defines a holding portion 156 of each of the trigger wires 150. The holding portions 156 extend through the apices of the bare stents 110, thereby retaining the apices of the bare stents 110 to the nose cone 102. As further described below, pulling on the trigger wires 150 to remove them from the nose cone 102 will cause the bare stents 110 to be released to expand outwardly.

The trigger wires 150 extend longitudinally along the perimeter of the stent-graft 112, as described above. The trigger wires 150 can be laterally held in place by suture loops 160, or other loop-like structure, disposed along the length of the stent 112, as well as by the loops 141 of the diameter reducing connectors 140. More specifically, the trigger wires 150 can be held laterally in place by ends 141a of the loops 141.

Figure 4:
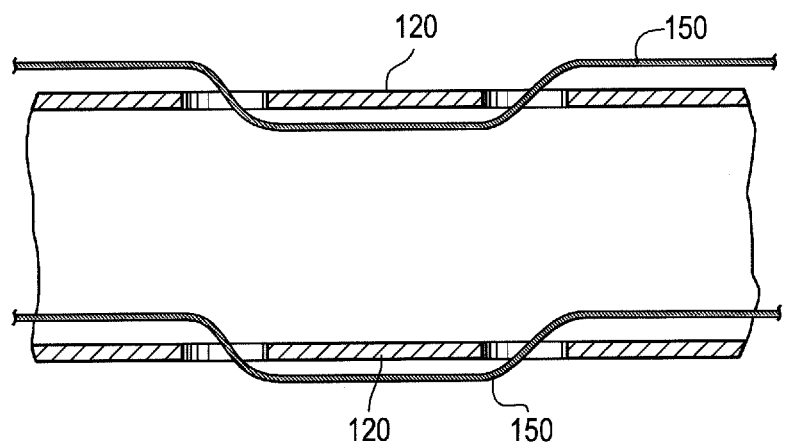
FIG. 4 is a side view of the trigger wires being threaded through graft material of the stent-graft.

In another form, as shown in FIG. 4, the trigger wires 150 can be threaded in and out of the graft material 120 in the longitudinal direction, thereby limiting the use of suture loops 160 attached to the stent-graft 112. In this form, the trigger wires 150 will still extend through the loops 141 of the diameter reducing connectors 140 as shown in FIGS. 1 and 2.

The stent-graft 112 can be configured to transfer from a compressed delivery state to an expanded installed state. Expansion of the stent-graft 112 will be described in further detail below. To compress the stent-graft 112 for delivery into the patient, the stent-graft 112 can be circumferentially compressed along its length for delivery in a manner known in the art.

The diameter reducing connectors 140 are attached around the circumference of the stent-graft 112 in the desired locations along the length of the stent-graft 112. The loops 141 are generally attached to the graft at their ends 141b via a suture or other known fixing mechanism for attaching a loop to graft material. The ends 141a of the loops 141 are coupled to each other via one of the trigger wires 150 extending through the ends 141a of circumferentially adjacent loops 141. When linked fully around the circumference of the stent-graft 112, the diameter of the diameter reducing connectors 140 is less than the diameter of the stent-graft 112 in its expanded state. Thus, by connecting each of the loops 141, the diameter of the stent-graft 112 is reduced. With the connectors 140 being attached to the stent-graft 112 around the stents 130 and/or 131, the stents 130 and 131 are likewise compressed. The stents 130 and 131, being self-expanding stents, will exert a radially outward force against the connectors 140 so that release of the connectors 140 will allow the stent-graft 112 to expand outwardly.

The stent-graft 112 can also be held in a compressed state by compressing the graft and inserting it into a sheath or other tubular member as known in the art. The distal legs 116 and 118, and the portion of the stent-graft 112 longitudinally adjacent thereto, can be generally compressed in this manner if diameter reducing connectors 140 are not used in these areas.

The bare stents 110 are compressed by bending them inward toward the nose cone 102. As described above, the bare stents 110 are retained at the nose cone 102 by the holding portions 156 defined by the trigger wires 150 between the housing 154 and the nose cone 102. The bare stents 110 are, similar to the stents 130 and 131, configured to expand radially outward, so the bare stents 110 will exert a radially outward force on the holding portion 156 and will expand outwardly upon release from the holding portions 156.

By running the trigger wires 150 along the perimeter of the stent-graft 112, the cannula 106 can be made relatively thin compared to a cannula that would include trigger wires extending therethrough for holding the bare stents. Thus, when the stent-graft 112 is compressed as described above, the stent-graft 112 can have a smaller compressed size relative to a graft having a thicker cannula. The smaller compressed diameter of stent-graft 112 can allow for a smaller overall delivery system, thereby reducing trauma to the patient during the procedure. When in the compressed condition, the stent-graft 112 will tend to have a folded wave-like cross-section as known in the art. In this condition, the trigger wires 150, extending along the perimeter of the stent-graft 112 instead of through the cannula 106, can be disposed within the folds of the compressed stent-graft 112, thereby generally not increasing the outer profile of the stent-graft 112.

Moreover, the use of the same trigger wires 150 for the bare stents 110 and the diameter reducing connectors 140 reduces the overall profile of the stent-graft 112, as well, because the number of total trigger wires is reduced.

With the trigger wires 150 extending from the nose cone 102 to the housing 154 and then to the perimeter of the stent-graft 112, the radially outward force of the stent-graft 112 that is exerted against the trigger wires 150 can cause the trigger wires 150 themselves to exert a radially outward force on the nose cone 102 and the housing 154. As such, the nose cone 102 and the housing 154 are preferably made from a material that has a low friction with the material of the trigger wire 150 to reduce the friction on the trigger wire 150 when it is pulled to release the bare stents 110.

In one preferred form, as shown in FIG. 10, the stent-graft 112 is constrained at its proximal region in the following configuration. The stent-graft 112 includes a stent 230 disposed on the outer surface of the stent-graft 112. A stent 231 is disposed proximally adjacent the stent 230 and is disposed on the inner surface of the stent-graft 112. A stent 232 is disposed at the proximal end of the stent-graft 112 and is also disposed on the inner surface of the stent-graft 112. One set of connectors 240 are disposed at the distal bends of the stent 230. Another set of connectors 241 are disposed at the middle of the stent 231. The stent 232 can be free from direct restraint by connectors.

The number of sets of connectors and the locations of the connectors on the stents defines the shape of the stent-graft 112, as shown in FIG. 10. The area of the stent-graft 112 between connectors 240 and 241 defines a reduced diameter portion 250. The area from the most proximal set of connectors 241 to the proximal end of the stent-graft 112 defines a tapered portion 260 that increases in diameter proximally.

In another preferred form, as shown in FIG. 11, the stent-graft 112 is constrained at its proximal region in the following configuration. The stent-graft 112 includes a stent 330 disposed on the outer surface of the stent-graft 112. A stent 331 is disposed proximally adjacent the stent 330 and is disposed on the inner surface of the stent-graft 112. A stent 332 is disposed at the proximal end of the stent-graft 112 and is also disposed on the inner surface of the stent-graft 112. One set of connectors 340 are disposed at the distal bends of the stent 230. A second set of connectors 341 are disposed at the middle of the stent 331. A third set of connectors 342 are disposed at middle of the stent 332.

The number of sets of connectors and the locations of the connectors on the stents defines the shape of the stent-graft 112, as shown in FIG. 11. The area of the stent-graft 112 between connectors 340 and 342 defines a reduced diameter portion 350, which is longer than reduced diameter portion 250 described above. The area from the most proximal set of connectors 342 to the proximal end of the stent-graft 112 defines a tapered portion 360 that increases in diameter proximally, and has a shorter length than tapered portion 260 described above.

In another preferred form, as shown in FIG. 12, the stent-graft 112 is constrained at its proximal region in the following configuration. The stent-graft 112 includes a stent 430 disposed on the outer surface of the stent-graft 112. A stent 431 is disposed proximally adjacent the stent 430 and is disposed on the outer surface of the stent-graft 112, as well. A stent 432 is disposed at the proximal end of the stent-graft 112 and is disposed on the inner surface of the stent-graft 112. One set of connectors 440 are disposed at the distal bends of the stent 230. A second set of connectors 441 are disposed at the middle of the stent 331. A third set of connectors 442 are disposed at distal end of the stent 432.

The number of sets of connectors and the locations of the connectors on the stents defines the shape of the stent-graft 112, as shown in FIG. 12. The area of the stent-graft 112 between connectors 440 and 442 defines a reduced diameter portion 350, which is longer than reduced diameter portion 250 and shorter than reduced diameter portion 350, described above. The area from the most proximal set of connectors 442 to the proximal end of the stent-graft 112 defines a tapered portion 460 that increases in diameter proximally, and has a shorter length than tapered portion 260 and a longer length than tapered portion 360 described above.

The above described stent-grafts 112 of FIGS. 10-12 can utilize the triggers wires 150 described above as well as the other delivery components described above, to constrain and thereafter release the stent-grafts shown in FIGS. 10-12.

It will be appreciated that other combinations of stents on the inside or outside of the stent-graft can be used, as well as the location on the stents where the connectors are disposed. Furthermore, the number of stents that can be constrained, as well as the number of connectors can also vary, depending on the needs of the user.

Having described the general structure of the stent-graft 112, the delivery and deployment of the stent-graft 112 will now be described.

FIGS. 5-9 illustrate a deployment process for the system 100. First, the delivery system 100 is inserted into a patient's vasculature percutaneously and advanced over a guidewire to the treatment site in the thoracic arch or the like using the Seldinger technique, which is well known in the art. The delivery system 100 may have radiopaque markers disposed on a retention sheath to indicate circumferential and longitudinal orientation of the delivery system 100.

Figure 5:
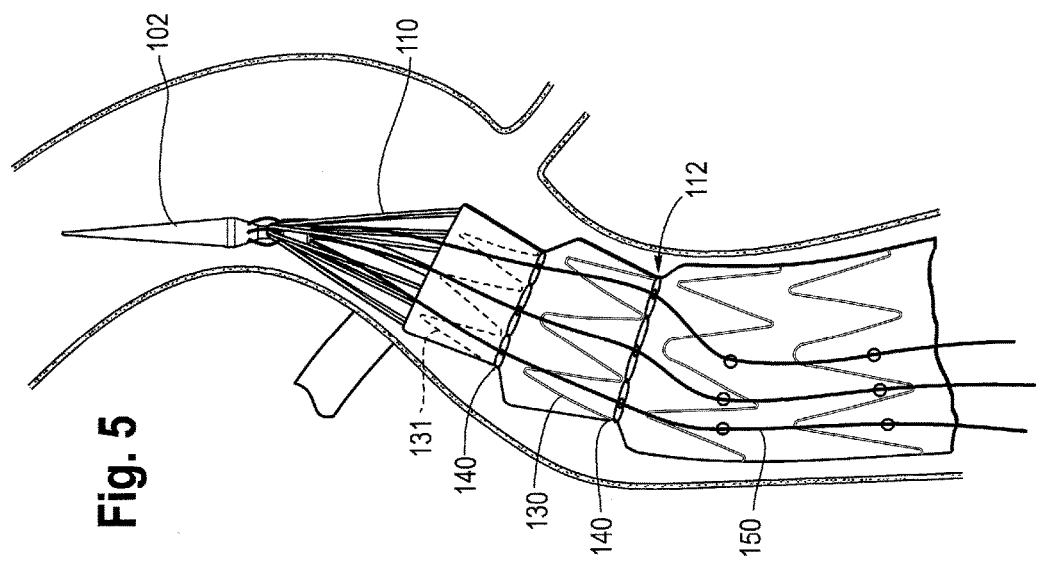

Initially, the stent-graft 112 is restrained in a reduced diameter, compressed or collapsed configuration against the cannula 106 by the retention sheath or the like. Once the delivery device 100 is advanced to the treatment site, the sheath is withdrawn and the proximal end of the stent-stent-graft 112 is allowed to expand partially outward against the vessel wall. Additionally, the bare stents 110 are exposed within the vessel. The sheath can be retracted further relative to the stent-graft 112, to expose the remainder of the stent-graft 112, as shown in FIG. 5.

The stent-graft 112 can then be expanded in a sequential manner due to the relationship between the trigger wires 150 and the stent-graft 112.

Figure 6:
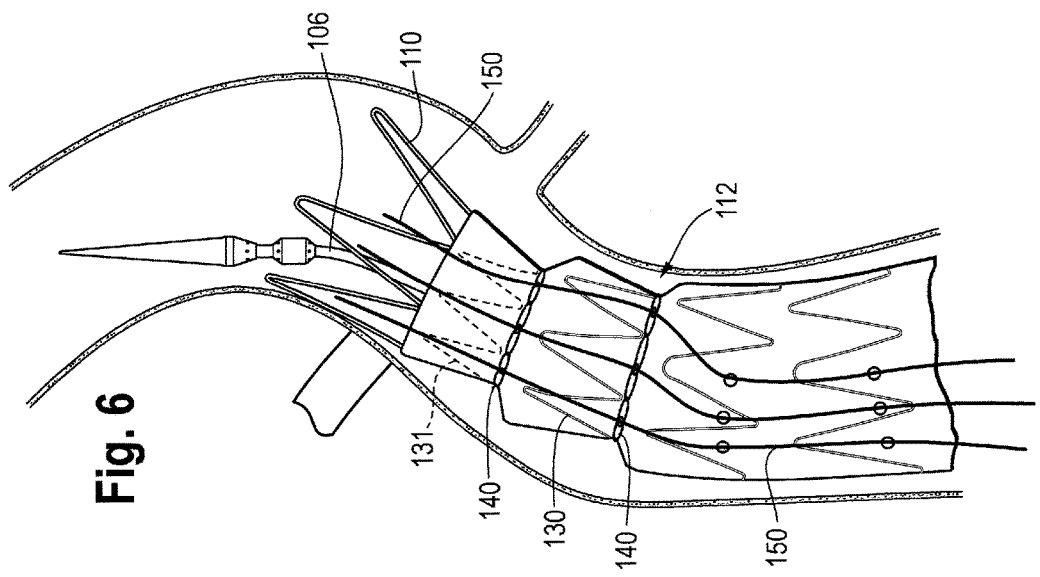

In one form, one of the trigger wires 150 can be retracted in the distal direction a first amount to release the bare stent 110 that is retained to the trigger wire 150 at the holding portion 156. The bare stent 110 that has been released will then expand radially outward and into engagement with the vessel wall. This can be repeated for the remainder of the trigger wires 150 to release the remainder of the bare stents 110, thereby allowing the remainder of the bare stents 110 to expand radially outward and into engagement with the vessel wall. By releasing the bare stents 110 in this manner, the bare stents 110 can anchor the stent-graft 112 to the vessel wall to limit migration of the stent-graft 112 within the vessel, as shown in FIGS. 6 and 7.

Following release of the bare stents 110, one of the trigger wires 150 can be retracted distally a second amount to release the loops 141 of the diameter reducing connector 140 longitudinally adjacent the bare stents 110, such as the connector 140 that is constraining the sealing stent 131. Releasing the loops 141 that are coupled to the trigger wire 150 will allow the loops 141 to become de-coupled to each other, allowing the stent-graft 112 to expand outward a first amount. This can be repeated for the remainder of the trigger wires 150 to release the remainder of the loops 141 that are constrained by these trigger wires. Thus, the stent-graft 112 will be allowed to expand radially outward in the area of the sealing stent 131 to engage the vessel wall in that area, as shown in FIG. 8.

Figure 9:
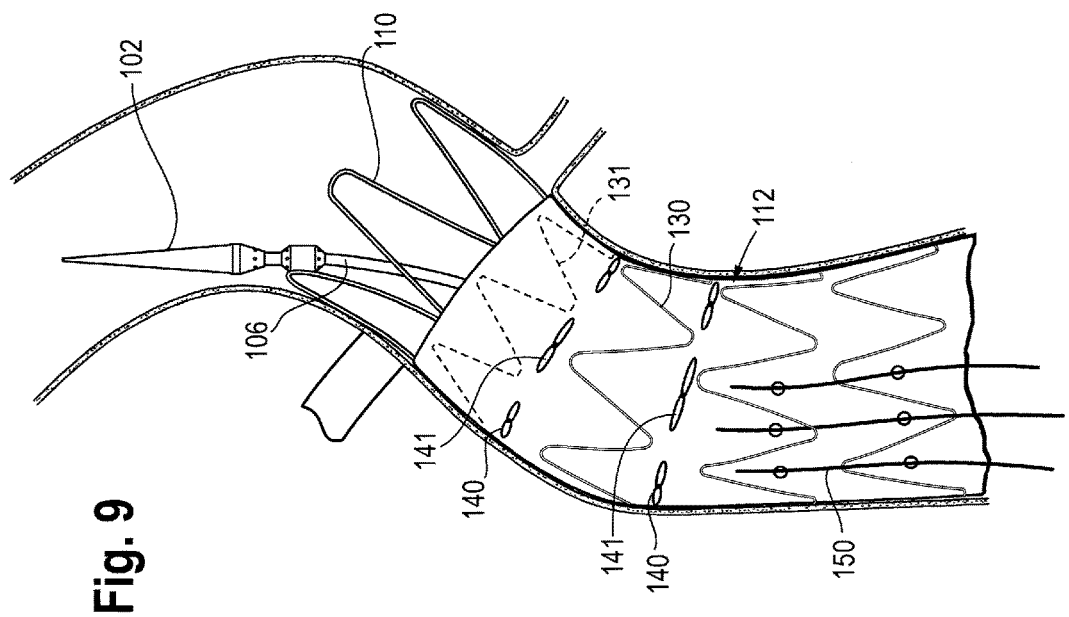

Following the release of the stent-graft 112 in the area of the sealing stent 131, one of the trigger wires 150 can be retracted distally an additional amount to release the loops 141 of the diameter reducing connector 140 located distally adjacent the sealing stent 131. Similar to the above, the stent-graft 112 will be expanded radially outward an additional amount in the location of the stent 130 that is constrained by the connector 140. The remainder of the trigger wires 150 can be sequentially retracted to release the remainder of the loops 141 to allow the stent-graft 112 to expand fully to engage the vessel wall in the area of stent 130, as shown in FIG. 9.

The above process can be repeated for any remaining stents 130 that are constrained. After each of the diameter reducing connectors 140 have been released and the stent-graft 112 has been expanded, the trigger wires 150 can be retracted fully and out of engagement with the stent-graft 112, leaving the stent-graft 112 engaged with the vessel wall.

With the stent-graft 112 engaged with the vessel wall and in the installed configuration, the catheter 104, cannula 106, and nose cone 102 can be retracted from the vessel, along with the guidewire 10 and any other non-graft structure. The percutaneous procedure can then be concluded in a manner known in the art.

In another form, rather than first expanding the bare stents 110 prior to expanding the sealing stent 131 and then the stent 130, the stent-graft 112 can be expanded along its length corresponding to individual trigger wires 150. For example, a single trigger wire 150 can be retracted along the length of the stent-graft 112, allowing the bare stent 110, sealing stent 131, and stent 130 to partially expand in the area of the retracted trigger wire 150. Following retraction of this trigger wire 150, another trigger wire 150 can be retracted, expanding the bare stent 110, sealing stent 131, and stent 130 an additional sequential amount. This can be repeated for the remainder of the trigger wires 150.

It will be appreciated that the various sequential retractions of the trigger wires 150 can be varied to suit the needs of the user, partially expanding the various portions of the stent-graft 112 by altering the order and distance in which the trigger wires 150 are retracted.

The trigger wires 150 can be retracted in any order. For example, the trigger wires 150 can be retracted such that circumferentially adjacent trigger wires 150 are released in order. Alternatively, one of the trigger wires 150 on one side of the stent-graft 112 can be retracted, followed by one of the trigger wires 150 on the opposite side of the stent-graft 112. It will be appreciated that various sequences of trigger retraction can be performed to suit the needs of the user.

In the case where the releasable bare stents 110 extend from the distal end of the stent-graft 112, withdrawing the trigger wires 150 can first allow the stents 130 and 131 to be released, followed by releasing the bare stents 110. It will be appreciated that similar modifications to the order of releasing the various components of the stent-graft can be realized by altering the positioning of the components along the length of the stent-graft 112, as well as altering the direction to withdraw the trigger wires 150, if desired.

While preferred embodiments have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the features described above are not necessarily the only features of the invention, and it is not necessarily expected that all of the described features will be achieved with every embodiment of the invention.

I claim:

1. A system for deploying a stent graft, the system comprising:
   a delivery device,
   an expandable stent graft comprising:
   a tubular body of graft material having a first end, a second end, a first portion adjacent the first end and extending toward the second end for a length, and a second portion adjacent the second end and extending toward the first end for a length;
   a series of stents attached to a surface of the tubular body of graft material from the first end to the second end;

a first of the series of stents extending away from the first end and having proximal and distal apices;

at least second and third stents of the series of stents disposed in the first portion;

at least fourth and fifth stents of the series of stents disposed in the second portion;

a first diameter reducing connector engaged at least partially about the second stent to reduce a diameter of the second stent;

a second diameter reducing connector engaged at least partially about the third stent to reduce a diameter of the third stent;

wherein the fourth and fifth stents remain unstrained by diameter reducing connectors;

at least one retractable trigger wire engaging a proximal apex of the first stent to retain the first stent to the delivery device, wherein the delivery device comprises an inner catheter having a first end, a nose cone at the first end of the inner catheter, a housing distal of the nose cone and adjacent the first end of the tubular body of graft material, and a holding region between the nose cone and the housing, wherein the proximal apices of the first stent extend over the housing and the at least one retractable trigger wire extends out of the housing, extends over the proximal apex of the first stent to retain the proximal apex of the first stent in the holding region, and then extends into the nose cone, wherein the at least one retractable trigger wire has a first length that extends from the first stent and engages the diameter reducing connectors of the at least second and third stents, and has a second length that extends over a surface of the second portion of the tubular body of graft material to past the second end of the expandable stent graft, whereupon retraction of the at least one retractable trigger wire, in sequence, the first stent expands, the second stent expands, and the third stent expands.

2. The system of claim 1, wherein the second length extends over an exterior surface of the second portion of the tubular body of graft material.

3. The system of claim 2, wherein the second length weaves in and out of the tubular body of graft material in the second portion.

4. The system of claim 1, further including loops on a surface of the second portion, where in the second length engages the loops.

5. The system of claim 4, wherein the loops are on an exterior surface of the second portion.

6. The system of claim 1, wherein the at least one retractable trigger wire comprises a plurality of trigger wires, wherein each of the plurality of trigger wires engages one or more proximal apices of the first stent.

7. The system of claim 1, wherein the diameter reducing connectors are disposed at a mid-portion of the at least second and third stents.

8. The system of claim 1, wherein the diameter reducing connectors engage distal apices of the at least second and third stents.

9. The system of claim 1, wherein a sixth stent is disposed in the first portion and a third diameter reducing connector is engaged to and reduces the diameter of the sixth stent.

* * * * *